United States Patent [19]
Tsai et al.

[11] Patent Number: 5,976,694
[45] Date of Patent: Nov. 2, 1999

[54] WATER-SENSITIVE COMPOSITIONS FOR IMPROVED PROCESSABILITY

[75] Inventors: Fu-Jya Tsai, Appleton; William S. Pomplun, Neenah; Pavneet S. Mumick, Appleton, all of Wis.

[73] Assignee: Kimberly-Clark Worldwide, Inc., Neenah, Wis.

[21] Appl. No.: 08/943,755

[22] Filed: Oct. 3, 1997

[51] Int. Cl.⁶ .................................................. D02G 3/00
[52] U.S. Cl. ........................................ 428/373; 428/374
[58] Field of Search ..................................... 428/373, 374

[56] References Cited

U.S. PATENT DOCUMENTS

| | | |
|---|---|---|
| 3,563,241 | 2/1971 | Evans et al. . |
| 3,670,731 | 6/1972 | Harmon . |
| 4,002,171 | 1/1977 | Taft . |
| 4,032,993 | 7/1977 | Coquard ........................................ 3/1 |
| 4,381,335 | 4/1983 | Okamoto . |
| 4,496,619 | 1/1985 | Okamoto . |
| 4,627,950 | 12/1986 | Matsui et al. . |
| 4,795,668 | 1/1989 | Krueger et al. . |
| 4,966,808 | 10/1990 | Kawano . |
| 5,057,368 | 10/1991 | Largman et al. . |
| 5,069,970 | 12/1991 | Largman et al. . |
| 5,097,004 | 3/1992 | Gallagher ................................ 528/272 |
| 5,097,005 | 3/1992 | Tietz ...................................... 528/372 |
| 5,108,820 | 4/1992 | Kaneko et al. . |
| 5,217,495 | 6/1993 | Kaplan ..................................... 623/13 |
| 5,219,646 | 6/1993 | Gallagher ................................ 428/287 |
| 5,277,976 | 1/1994 | Hogle et al. . |
| 5,304,420 | 4/1994 | Hirakawa et al. . |
| 5,312,883 | 5/1994 | Komatsu et al. . |
| 5,366,804 | 11/1994 | Dugan . |
| 5,382,400 | 1/1995 | Pike et al. . |
| 5,407,442 | 4/1995 | Karapasha . |
| 5,466,410 | 11/1995 | Hills . |
| 5,470,941 | 11/1995 | Kim et al. . |
| 5,593,778 | 1/1997 | Kondo ..................................... 428/373 |
| 5,698,322 | 12/1997 | Tsai et al. ............................... 428/373 |

FOREIGN PATENT DOCUMENTS

| | | |
|---|---|---|
| 0 569 145 A2 | 11/1993 | European Pat. Off. . |
| 0 648 871 A1 | 4/1995 | European Pat. Off. . |
| 0 761 795 A2 | 3/1997 | European Pat. Off. . |
| 5125123 | 5/1993 | Japan . |
| WO 93/07199 | 4/1993 | WIPO . |
| 95//18191 | 7/1995 | WIPO . |
| 97/02375 | 1/1997 | WIPO . |
| 98/36117 | 8/1998 | WIPO . |

OTHER PUBLICATIONS

JP 06–207324 (Unitika Ltd.) (7/26/94), *Patent Abstracts of Japan*, vol. 18, no. 571 (C–1267), 2 Nov. 1994.

*Primary Examiner*—Newton Edwards
*Attorney, Agent, or Firm*—James & Askew, LLP

[57] ABSTRACT

The present invention is directed to thermoformable ion-sensitive compositions having improved processability. In addition, the present invention is directed to a process of making water-dispersible fibers, films and fabrics, which maintain their structural integrity and strength when in use, but dissolve and disperse when placed in contact with large amounts of water, such as in a conventional sink or toilet. Moreover, the present invention is directed to water-dispersible products, including flushable products such as personal care products, diapers, incontinence devices, release liners, feminine napkins, product packaging, etc., which contain fibers, films and fabrics formed from the water-sensitive compositions.

22 Claims, No Drawings

WATER-SENSITIVE COMPOSITIONS FOR IMPROVED PROCESSABILITY

FIELD OF THE INVENTION

The present invention is directed to water-sensitive compositions having improved processability. In addition, the present invention is directed to a process of making water-dispersible thermoformable articles, such as fibers, films and fabrics, which maintain their integrity and strength when in use, but dissolve and disperse when placed in contact with large amounts of water, such as in a conventional toilet. Moreover, the present invention is directed to water-dispersible products, including flushable products such as personal care products, diapers, feminine napkins, wipes, incontinence products, release liners, product packaging, etc., which contain the above-mentioned fibers, films and fabrics.

BACKGROUND OF THE INVENTION

Disposable products have revolutionized modern lifestyle and are of great convenience to society. Such products generally are relatively inexpensive, sanitary and quick and easy to use. Disposal of such products, however, is a concern as landfills close and incineration contributes to urban smog and pollution. Consequently, there is an urgent need for disposable products that can be disposed of without dumping or incineration. An ideal disposal alternative would be the use of municipal sewage treatment plants and private residential septic systems. Products suited for disposal in sewage systems that can be flushed down a conventional toilet are termed "flushable." An essential feature of flushable products is that they must have sufficient wet strength for their intended use, yet lose structural integrity upon contact with water.

Numerous attempts have been made to produce flushable fibers, fabrics, films and adhesives that retain their integrity and wet strength during use, yet can be disposed of via flushing in conventional toilets. One approach to producing a flushable product is to limit the size of the product so that it will readily pass through plumbing without causing obstructions or blockages. Such products have high wet strength, yet do not disintegrate during flushing. Examples of this type of product include wipes such as baby wipes. This approach to flushability suffers the disadvantage, however, of being restricted to small sized articles. Many of the current flushable products are limited to such small articles.

Another approach to producing a flushable product is to manufacture a product that is normally insoluble in water, but which disintegrates in the presence of alkaline or acidic aqueous solutions. The end user is provided with an alkaline or acidic material to add to the water in which the product is to be disposed. This approach permits disposal via normal plumbing systems of products substantially larger than wipes, but suffers from the disadvantage of forcing the user to perform the step of adding the dissolving chemical to the water. A further disadvantage is that the inadvertent or unintentional disposal of such a product in a conventional toilet without the addition of the dissolving chemical can cause serious obstruction or blockage of the plumbing system. The latter disadvantage can, however, be overcome by incorporating the dissolving acid or alkali into the article but separate from the dissolvable material while in use. The dissolving chemical is only released upon contact with water during flushing.

Another approach to producing a flushable product is to prepare products such as fibers, fabrics and films from water soluble materials. Upon contact with water, the water soluble material dissolves, reducing the structural integrity of the product, and causing its disintegration, such that it will easily pass through the plumbing system. Although the products prepared by this approach are suitable for dry applications wherein the product does not come in contact with any aqueous solution, these products are not suited for applications, such as personal care products, wherein the product may come into contact with even a relatively small amount of aqueous solution.

One approach to producing thermoformable articles for use in personal care products, which can withstand prolonged contact with body fluids, such as blood, urine, and perspiration, has been the use of "ion triggerable" polymeric materials. Such "ion triggerable" polymeric materials remain stable when in contact with aqueous solutions having a relatively high ion concentration, but dissolve and disperse when placed in contact with aqueous solutions having a relatively low ion concentration, such as ordinary tap water. In other words, the polymeric materials possess "water triggerability." Ion triggerable polymeric materials have been used as binders for nonwoven webs and also as a thermoformable material. For example, a salt sensitive water soluble polyurethane binder for flushable nonwoven fabrics is disclosed in U.S. Pat. No. 4,002,171, issued to Taft. Further, a salt sensitive water soluble terpolymer for making flushable paper diapers, bandages and sanitary towels is disclosed in Japanese Patent No. JP 5125123 and U.S. Pat. No. 5,312,883 assigned to LION Corp.

A more recent approach to forming ion triggerable articles is described in U.S. patent application Ser. No. 08/730,951, assigned to Kimberly-Clark Worldwide, the assignee of the present invention. In U.S. patent application Ser. No. 08/730,951, thermoformable articles are prepared from ion triggerable materials. A preferred ion triggerable material, a copolyester which dissolves and disperses in tap water in no more than 60 minutes, offers good water responsiveness. However, the copolyester exhibits processability constraints. Typically, the copolyester has poor melt strength, is very sticky, and is very difficult to stretch into a fine fiber without breaking. Past efforts have been made to try to improve the processability of the copolyester, but have failed. The resulting fibers possess a melt strength that is not high enough to ensure good fiber processing into a desirable denier range (less than 7 denier per fiber). In addition, silicone oil based finishing agents were required to avoid the stickiness of the resulting fibers, which can affect adhesion properties of binder fibers.

What is needed in the art is a method of improving the processability of existing water-sensitive polymeric materials. Also, what is needed in the art is water-sensitive thermoformable articles having improved processability wherein the articles maintain structural integrity when exposed to ionic aqueous solutions, such as body fluids, yet readily disperse when flushed down a conventional toilet. Further, what is needed in the art is personal care products comprising thermoformable articles having improved processability wherein the personal care products maintain structural integrity when exposed to body fluids, such as blood, urine, perspiration, and other body fluids, yet readily disperse when flushed down a conventional toilet.

SUMMARY OF THE INVENTION

The present invention is directed to unique compositions which provide significantly improved processability. The compositions comprise a blend of at least one water-sensitive polymer and at least one polymer selected from polylactide (PLA), polyolefin-grafted with one or more polar groups, such as maleic anhydride (MA), and other aliphatic polyesters. Desirably, the water-sensitive polymer comprises one or more copolyesters. The compositions may be spun into monocomponent or multicomponent fibers through conventional processes, such as spunbonding and meltblowing processes. The compositions may also be extruded to form films and other thermoformable articles.

The present invention is also directed to multicomponent fibers, such as sheath/core fibers, wherein the compositions described above are present on an outer surface of the multicomponent fiber. In sheath/core multicomponent fiber applications, the composition in the sheath structure has "ion triggerability" which allows water to dissolve the sheath material, while the core materials are polymeric materials, such as polyolefins, which provide processing and binding strength and reduce the fiber cost. Other heteromorphic multicomponent fiber configurations suitable for the present invention include, but are not limited to, side-by-side, pie-shape, and island-in-the-sea fiber configurations. The resulting fibers may be used to form air-laid nonwovens for use as coverstock, liners or absorbent webs in a variety of products including, but not limited to, personal care products.

The compositions of the present invention may also be used as a coating or co-extruded component of a flushable film for applications in composite cloth-like outercover for flushable diapers, or as a baffle barrier film for feminine care napkins and adult incontinence products. The present invention has broad applicability for any single use flushable product requiring a barrier film, spun fiber, absorbent core, or any combination thereof.

DETAILED DESCRIPTION OF THE INVENTION

The present invention overcomes the previously mentioned processability problems associated with the production of thermoformable articles comprising water-sensitive polymers. The compositions of the present invention not only significantly improve processability, but also maintain water triggerability. In the case of fibers, the improved processability is evidenced by a maximum jet stretching ratio and a reduction in fiber stickiness. In general, the compositions of the present invention comprise at least one water-sensitive polymer, desirably a copolyester, and at least one additional polymer selected from polylactide (PLA), polyolefin-grafted with one or more polar groups, such as maleic anhydride (MA), and other aliphatic polyesters.

Suitable water-sensitive polymers for the compositions of the present invention include polymers which remain stable when in contact with aqueous solutions having a relatively high ion concentration, but dissolve and disperse when placed in contact with aqueous solutions having a relatively low ion concentration, such as ordinary tap water. Typically, the polymer contains one or more ion sensitive functional group, such as sulfonate and carboxylate groups. Polymers for use in the present invention include, but are not limited to, copolyesters available from National Starch and Chemical Company under the product designations NS 70-4395 and NS 70-4442; copolyesters available from Eastman Chemical Company (Kingsport, Tenn.) under the product designations AQ29S, AQ38S, AQ55S, AQ1350 and AQ1950; and copolymers and terpolymers of acrylic acids and/or acrylate esters, such as those available from Lion Corporation (Tokyo, Japan) or Belland (Switzerland). Particularly suitable polymers include the NS 70-4395 and NS 70-4442 copolyesters available from National Starch and Chemical Company.

The compositions of the present invention also contain at least one additional polymer selected from polylactide (PLA), polyolefin-grafted with one or more polar groups, such as maleic anhydride (MA), and other aliphatic polyesters. As used herein, the term "polylactide" includes the polylactide polymer and copolymers thereof, such as a copolymer of optical isomers of lactide or copolymers such as lactide and caprolactone copolymers. Suitable polyolefins to be grafted with one or more polar groups include, but are not limited to, polyethylene, polypropylene, ethylene-propylene copolymers, and polybutylene. Suitable polar groups for grafting onto the polyolefin polymer chain include, but are not limited to, maleic anhydride (MA), polyethylene glycol (PEG), polyethylene glycol methacrylate (PEGMA), hydroxyethyl methacrylate (HEMA), 2-ethylhexyl methacrylate (EHMA), vinyl alcohol, vinyl acetate, and other polar groups. Suitable other aliphatic polyesters include, but are not limited to, polybutylene succinate, polybutylene succinate-co-adipate, polycaprolactone, SKYGREEN™ (See U.S. Pat. No. 5,470,941; assigned to Sunkyoung Industries), and blends of the above-mentioned polymers. Desirably, the at least one additional polymer component is a polyester having good compatibility with the water-sensitive polymer. More desirably, the at least one additional polymer component is a polylactide copolymer having a similar melt viscosity to the water-sensitive polymer.

The weight ratio of the water-sensitive polymer to the polylactide (PLA), polyolefin-grafted with one or more polar groups, or other aliphatic polyesters, may vary greatly; however, certain applications, such as fine fibers, may require a particular weight ratio. Desirably, the weight ratio of water-sensitive polymer to the at least one additional polymer component is from about 60:40 to about 90:10. More desirably, the weight ratio of copolyester to the at least one additional polymer component is from about 70:30 to about 90:10. More desirably, the weight ratio of water-sensitive polymer to the at least one additional polymer component is from about 75:25 to about 85:15. When the weight ratio of water-sensitive polymer to the at least one additional polymer component is less than about 60:40, the composition exhibits less than desirable ion triggerability and flushability for personal care products. When the weight ratio of water-sensitive polymer to the at least one additional polymer component is greater than about 90:10, the composition exhibits potential processability difficulty, especially in the case of the composition being spun into fine fibers. Table 1 below lists the properties of various fibers comprising compositions of the present invention and unmodified fibers (i.e., fibers comprising a copolyester without processability-enhancing additives).

TABLE 1

| Polymer Type | Viscosity (Pa · s) at 180 C., 1000s⁻¹ | Process-ability (maximum jet stretch ratio)* | Process-ability (stickiness) | Minimum Denier Achieved (dpf) | Urine Stability | Water Dispersability |
|---|---|---|---|---|---|---|
| NS 70-4442 100 | 28.7 | poor (29) | very sticky | 8.0 | fair | excellent |
| NS 70-4442/ PLA (PLX5-2) 70/30 | 76.7 | good (180) | none | 1.3 | excellent | poor |
| NS 70-4442/ PLA 75/25 | 72.7 | good (180) | none | 1.3 | excellent | fair |
| NS 70-4442/ PLA 80/20 | 62.3 | good (180) | none | 1.8 | good | fair |
| NS 70-4442/ PLA 85/15 | 54.8 | good (128) | none | 1.8 | good | good |
| NS 70-4442/ PP grafted MA 70/30 | 52.1 | fair (102) | none | 2.3 | excellent | fair |

*The maximum jet stretch ratio (MJSR) is the ratio of the fiber take-up rate to the linear extrusion rate.

The water-sensitive composition of the present invention may be thermoformed into a variety of articles including, but not limited to, fibers, fabrics, films and absorbents. The water-sensitive composition can be spun into monocomponent fibers or multicomponent fibers. As used herein, the term "monocomponent fiber" means a fiber formed solely from the water-sensitive composition of the present invention. As used herein, the term "multicomponent fiber" means a fiber formed from the water-sensitive composition of the present invention and at least one other material. The water-sensitive fibers may be formed using any conventional fiber forming process including, but not limited to, melt-blowing and spunbonding processes. The fibers may be continuous or discontinuous. Continuous fibers may be formed by any spinning operation. Continuous fibers may be cut to form discontinuous fibers having suitable lengths for nonwoven processes such as carding (approximate length of 25 to 45 mm) or air-laying (approximate length of 0.2 to 15 mm).

In one embodiment of the present invention, the water-sensitive composition may be thermoformed into multicomponent fibers, such as sheath/core fibers, wherein the water-sensitive compositions described above are present on at least a portion of the outer surface of the multicomponent fiber. Desirably, the multicomponent fibers are bicomponent fibers wherein the water-sensitive composition of the present invention occupies at least a portion of the outer surface of the fiber and at least one additional material occupies the remainder of the fiber. More desirably, the bicomponent fiber has a sheath/core structure wherein the water-sensitive composition of the present invention forms the sheath, and a second material, such as a polymer having a melting temperature about 20° C. or greater than the melting temperature of the sheath material, forms the core. Most desirably, the bicomponent fiber has a sheath/core structure wherein the water-sensitive composition of the present invention forms the sheath, and the core material is polypropylene (PP), polyethylene (PE), or a combination thereof. In sheath/core multicomponent fiber applications, the composition in the sheath structure has "ion triggerability" which allows water to dissolve the sheath material, while the core materials are polymeric materials, such as polyolefins, which provide improved processing and binding strength and reduce the fiber cost. Although a concentric sheath/core fiber structure is a desirable embodiment, any other heteromorphic fiber configuration may be used including, but not limited to, pie shape, side-by-side, and island-in-the-sea etc., to achieve different degrees of triggerability, mechanical and tactile properties depending on the end use of the water-sensitive fibers. For flushable fiber applications, desirably the water-sensitive composition represents a continuous phase through the fiber so that the fiber disperses when placed in a conventional toilet.

The water-sensitive fibers of the present invention may be used alone or combined with other fibrous materials to form nonwoven, as well as, woven fabrics. In one embodiment of the present invention, the water-sensitive fibers of the present invention are useful as binder fibers alone or in combination with other fibrous material to form a nonwoven web. Other fibrous materials for use with the water-sensitive fibers of the present invention include natural fibers, synthetic fibers, and combinations thereof. The choice of fibers depends upon, for example, fiber cost and the intended end use of the finished fabric. For instance, suitable fabrics may include the water-sensitive fibers of the present invention and natural fibers including, but not limited to, cotton, linen, jute, hemp, wool, and wood pulp. Similarly, regenerated cellulosic fibers such as viscose rayon and cuprammonium rayon, modified cellulosic fibers, such as cellulose acetate, or synthetic fibers such as those derived from polyvinyl alcohol, polyesters, polyamides, polyacrylics, etc., alone or in combination with one another, may likewise be used in combination with the water-sensitive fibers of the present invention.

Depending on the end use of the finished fabric, the fiber length may be important in producing the fabrics of the present invention. In some embodiments such as flushable products, fiber length is of more importance. The minimum length of the fibers depends on the method selected for forming the fibrous substrate. For example, where the fibrous substrate is formed by carding, the length of the fiber should usually be at least about 30 mm in order to insure uniformity. Where the fibrous substrate is formed by air-laid or wet-laid processes, the fiber length may desirably be about 0.2 to 15 mm, more desirably about 0.2 to 6 mm. Although fibers having a length of greater than 50 mm are within the scope of the present invention, it has been determined that when a substantial quantity of fibers having a length greater than about 15 mm is placed in a flushable fabric, though the fibers will disperse and separate in water, their length tends to form "ropes" of fibers which can become entangled in home lateral piping obstructions, such as tree roots or bends in the piping. Therefore, for these products, it is desired that the fiber length be about 15 mm or less so that the fibers will not have a tendency to "rope" when they are flushed through a toilet. Although fibers of various length are applicable in the present invention, desirably fibers are of a length less than about 15 mm so that the fibers separate easily from one another when in contact with water, most desirably ranging from about 0.2 mm to about 6 mm in length.

Nonwoven fabrics containing the water-sensitive fibers of the present invention may be formed from a single layer or multiple layers. In the case of multiple layers, the layers are generally positioned in a juxtaposed or surface-to-surface relationship and all or a portion of the layers may be bound to adjacent layers. The nonwoven fabrics may also be formed from a plurality of separate nonwoven webs wherein the separate nonwoven webs may be formed from single or multiple layers. In those instances where the nonwoven web includes multiple layers, one or more of the multiple layers may contain water-sensitive fibers of the present invention.

The water-sensitive fibers of the present invention, alone or in combination with one or more additional fibers, are particularly useful for forming air-laid nonwoven fabrics. Air-laid fabrics find particularly useful application as bodyside liners, fluid distribution materials, fluid in-take materials (surge), cover stock and absorbent structures for various water-dispersible personal care products. The basis weights for these air-laid nonwoven fabrics will usually range from about 10 to about 200 gram per square meter (gsm). Short fibers of length less than about 15 mm are desirably used to make these flushable products. Surge or in-take materials need better resiliency and higher loft so at least some of the fibers in these air-laid nonwoven fabrics have a fiber titre of about 3 denier (d) or greater, more desirably about 6 denier (d) or greater. A desirable final density for the surge or in-take materials is between about 0.025 and about 0.050 grams per cubic centimeter (g/cc). Fluid distribution materials will have a higher density, in the desired range of about 0.10 to about 0.20 g/cc using at least some fibers of lower denier, most desirably, at least some fibers having a denier of about 3 d or less.

The water-sensitive compositions of the present invention may also be used in cast film and/or blown film applications. Films formed from the water-sensitive compositions of the present invention may be made entirely of the water-sensitive composition of the present invention or may contain the water-sensitive composition, as well as, other polymeric materials. Additionally, films may also be made by mixing various water-sensitive compositions. Desirably, the resulting film will contain a continuous phase of one or more water-sensitive compositions so that the film will disperse when placed in contact with water. Desirably, films formed from the water-sensitive composition of the present invention comprise at least 50 vol % of the water-sensitive composition of the present invention. More desirably, films formed from the water-sensitive composition of the present invention comprise from about 50 to about 90 vol % of the water-sensitive composition of the present invention. Most desirably, films formed from the water-sensitive composition of the present invention comprise from about 70 to about 90 vol % of the water-sensitive composition of the present invention.

The thickness of the film may vary greatly depending upon the end use of the film-containing product. Film thickness should be minimized when possible to reduce product cost and to reduce the time necessary for the film to disperse, especially in the case of flushable products. Desirably, the film thickness will be less than about 2.0 mil (50.8 micrometers). More desirably, the water-soluble film thickness will be from about 0.1 mil (2.54 micrometers) to about 1.0 mil (25.4 micrometers). Most desirably, the water-soluble film thickness will be from about 0.3 mil (7.62 micrometers) to about 1.0 mil (25.4 micrometers).

In one embodiment of the present invention, films formed from the water-sensitive composition of the present invention may be combined with one or more additional polymer films to impart specific mechanical, biodegradable, barrier and/or tactile properties to the film combination. Desirably, at least one film formed from the water-sensitive composition of the present invention is co-extruded with one or more additional polymer films to form a composite film.

In some embodiments, it may be desirable to incorporate one or more additives into the water-sensitive composition of the present invention. One or more additives may be added to the water-sensitive composition of the present invention to aid in the melt-processing applications described above. It should be noted that although fibers and films are desirable products formed from the water-sensitive composition of the present invention, other articles of manufacture may also be produced from the water-sensitive composition of the present invention. Such articles include, but are not limited to, compression molded articles, blow molded articles, injection molded articles, foam sheets and coated articles. Additives may be used in any of the above-mentioned articles. Further, additives may be used to provide one or more desired properties to articles formed from the water-sensitive composition of the present invention. Suitable additives include, but are not limited to, compatibilizers, processing aids, dispersants, slip agents, thickening agents, anti-foaming agents, and anti-microbial agents, antioxidants, as fabricating agents or as modifiers depending on the specific properties desired in the final product.

The fabrics and films of the present invention may be incorporated into such body fluid absorbent products as sanitary napkins, diapers, surgical dressings, tissues, wet wipes, incontinence devices and the like. These products may include an absorbent core, comprising one or more layers of an absorbent fibrous material. The core may also comprise one or more layers of a fluid-pervious element, such as fibrous tissue, gauze, plastic netting, etc. These are generally useful as wrapping materials to hold the components of the core together. Additionally, the core may comprise a fluid-impervious element or barrier means to preclude the passage of fluid through the core and on the outer surfaces of the product. Preferably, the barrier means also is water-dispersible. A film of a polymer having substantially the same composition as the aforesaid water-sensitive composition is particularly well-suited for this purpose. In accordance with the present invention, the polymer compositions are useful for forming each of the above-mentioned product components including the layers of absorbent core, the fluid-pervious element, the wrapping materials, and the fluid-impervious element or barrier means.

Those skilled in the art will readily understand that the water-sensitive compositions of the present invention may be advantageously employed in the preparation of a wide variety of products designed to withstand contact with salt solutions, yet disperse in large amounts of water. Such products may only comprise a single layer of the water-sensitive composition in the form of a layer of fibers, a film or a fabric, or may comprise the water-sensitive composition in the form of a layer of fibers, a film or a fabric in combination with one or more additional layers such as coatings, films, fabrics, etc. Although the water-sensitive composition and articles formed therefrom of the present invention are particularly suited for personal care products, the water-sensitive composition and articles formed therefrom of the present invention may be advantageously employed in the preparation of a wide variety of consumer products other than personal care products.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

(Control, Non-modified)

A copolyester from National Starch, NS 70-4442, was spun using a Kimberly-Clark laboratory fiber spinning line. The spinning line consisted of a ¾" (1.905 cm) diameter, 24:1 length to diameter ratio extruder with 3 heating zones, which feeds into a spin pump, through a ¾" (1.905 cm) KOCH®SMX static mixer unit, and then into the spinning head. Fibers were spun through 15 holes of 20 mil (0.508 mm) diameter. The fibers were quenched at 17° C. and drawn down to where it was either formed directly into a nonwoven or collected for further processing (i.e., crimping and cutting for production of staple and short-cut fibers) before being formed into a nonwoven.

The resulting fibers had very poor melt strength, as evidenced by a very low maximum jet stretch ratio (MJS=29 as listed in the Table). In addition, the resulting fibers had a tendency to stick together even at room temperature due to the high sensitivity to moisture and adhesive properties, making fiber handling very difficult.

EXAMPLE 2

(Monocomponent Fiber 75:25)

A blend of copolyester NS 70-4442 and a polylactide (CPX 5-2, a copolymer containing 95:5 levorotary (L):dextrorotary (D) isomers of PLA from Chronopol) was compounded at a 75:25 weight ratio in a twin screw-extruder. The resin blend was extruded into fibers using a Kimberly-Clark laboratory fiber spinning line as described in Example 1. Fibers were spun through 15 holes of 20 mil (0.508 mm) diameter. The fibers were quenched at 17° C. and drawn down to where it was either formed directly into a nonwoven or collected for further processing (i.e., crimping and cutting for production of staple and short-cut fibers) before being formed into a nonwoven.

The above 75:25 blend processed much better than the 100 wt % NS 70-4442 of Example 1 due to the blend's improved melt strength, as evidenced by significantly improved maximum jet stretch ratio (MJS=180 as listed in the Table), reduced stickiness, and reduced moisture sensitivity. The resulting fibers retained integrity in a 1 wt % sodium sulfate solution and lost significant strength in deionized water.

One possible mechanism for the improved stability in sodium sulfate solution is that sodium ions bind to the sulfonate groups of the ion-sensitive copolyester, thereby reducing the hydrophilicity of these groups on the polymer. At the same time, the sulfate ions structure the water molecules such that the hydrophobic parts of the copolyester are squeezed out of the water, increasing interpolymer interactions and reducing solubility. These two mechanisms together stabilize the polymer in sodium sulfate solution, or other salt solutions, with subsequent dissolution/dispersion in excess tap water.

EXAMPLE 3

(Monocomponent Fiber 80:20)

A blend of copolyester NS 70-4442 and PLA (CPX 5-2) was compounded at a 80:20 weight ratio in a twin screw-extruder. The resin blend was extruded into fiber using a Kimberly-Clark laboratory fiber spinning line as described in Example 1. Fibers were spun through 15 holes of 20 mil (0.508 mm) diameter. The fibers were quenched at 17° C. and drawn down to where it was either formed directly into a nonwoven or collected for further processing (i.e., crimping and cutting for production of staple and short-cut fibers) before being formed into a nonwoven.

As in Example 2, the 80:20 blend processed much better than the 100 wt % NS 70-4442 of Example 1 due to the blend's improved melt strength, as evidenced by significantly improved maximum jet stretch ratio (MJS=180 as listed in the Table), reduced stickiness, and reduced moisture sensitivity. The resulting fibers retained integrity in a 1 wt % sodium sulfate solution and lost significant strength in deionized water.

EXAMPLE 4

(Bicomponent 75:25)

A blend of copolyester NS 70-4442 and PLA (CPX 5-2) was compounded at a 75:25 weight ratio in a twin screw-extruder. Bicomponent fibers with a core/sheath (1/1) structure were prepared by using the blend as the sheath material and polypropylene (PP) having a melt flow rate of 80 g/10 min, from Chisso Corporation (Osaka, Japan), as the core material. Fiber spinning was conducted on a bicomponent spinning line using two identical extruders having specifications identical to those described above in Examples 1–3. The fiber components were fed into a sheath/core bicomponent spin pack and spun through 12 mil (0.305 mm) diameter holes. Likewise, the fibers were quenched and drawn down at 17° C. to where it was either formed into a nonwoven or collected for further processing (i.e., crimping and cutting for production of staple and short-cut fibers) before being formed into a nonwoven.

The 75:25 blend processed much better due to its improved melt strength, as evidenced by a significantly improved maximum jet stretch ratio (MJS=105), reduced stickiness, and reduced moisture sensitivity as compared with the fibers of Example 1 made with 100% NS 70-4442. Less sensitivity to moisture and reduced stickiness made the fibers much easier to handle during processing.

EXAMPLE 5

(Bicomponent Fiber 80:20)

A blend of copolyester NS 70-4442 and PLA (CPX 5-2) was compounded at a 80:20 weight ratio in a twin screw-extruder. Bicomponent fibers with a core/sheath (1/1) structure were prepared by using the blend as the sheath material and polypropylene (PP) having a melt flow rate of 80 g/10 min, from Chisso Corporation, as the core material. Fiber spinning was conducted on a bicomponent spinning line using two identical extruders as described above in Example 4. The fiber components were fed into a sheath/core bicomponent spin pack and spun through 12 mil (0.305 mm) diameter holes. Likewise, the fibers were quenched and drawn down at 17° C. to where it was either formed into a nonwoven or collected for further processing (i.e., crimping and cutting for production of staple and short-cut fibers) before being formed into a nonwoven.

The 80:20 blend processed much better due to its improved melt strength, as evidenced by a significantly improved maximum jet stretch ratio (MJS=105), reduced stickiness, and reduced moisture sensitivity as compared with the fibers of Example 1 made with 100% NS 70-4442. Less sensitivity to moisture and reduced stickiness made the fibers much easier to handle during processing.

EXAMPLE 6

(Bicomponent Fiber, Non-Modified, Large Scale)

Bicomponent fiber with core/sheath (1/1) structure was prepared by using copolyester NS 70-4442 as the sheath material and polypropylene having a melt flow rate of 80 g/10 min (Chisso Corporation) as the core material. Fiber spinning was conducted on a bicomponent spinning line using two identical extruders, feeding into a sheath/core bicomponent spin pack and through 350 holes of 0.6 mm diameter. The fibers were quenched and drawn down at 17° C. The fiber bundle passed through a finishing agent bath containing Dow Corning 200, a polydimethylsiloxane having a viscosity of 200 centistokes. The fiber bundle was then collected for further processing (i.e., crimping and cutting for production of staple and short-cut fibers) before being formed into a nonwoven. The resulting fibers had a tendency to stick together even at room temperature due to the high sensitivity to moisture and adhesive properties, making fiber handling very difficult and making crimping processing impossible. The finest non-crimped fiber produced was 7.9 dpf.

EXAMPLE 7

(Bicomponent Fiber blend 80:20, large scale)

A blend of copolyester NS 70-4442 and PLA (CPX 5-2) in a 80:20 ratio was compounded with a twin-screw extruder. Bicomponent fibers with a sheath/core (1/1) structure were prepared using this blend as the sheath component and polypropylene having a melt flow rate of 80 g/10 min (Chisso Corporation) as the core material. The spinning was conducted on a pilot scale bicomponent spinning line using two identical extruders, having the same specifications identified in Example 6, feeding into a sheath/core bicomponent spin pack and through 350 holes of 0.6 mm diameter. Likewise, the fibers were quenched and drawn down at 17° C. The resulting fibers did not stick together as in Example 6. At this point, the fiber bundle was optionally passed through a finish agent bath, for example, a bath containing Dow Corning 200. The fiber bundle was then collected for further processing (i.e., crimping and cutting for production of staple and short-cut fibers) before being formed into a nonwoven. The blend processed much better due to its improved melt strength, as evidenced by significantly improved maximum jet stretch ratio, reduced stickiness, and reduced moisture sensitivity as compared with fibers made with 100% NS 70-4442. Lessened sensitivity to moisture and reduced adhesive properties made the fibers much easier to handle during processing. The resulting fibers were able to be crimped and drawn to about 3.5 dpf.

EXAMPLE 8

A blend of copolyester NS 70-4442 and PLA (CPX 5-2) in a 80:20 ratio was compounded with a twin-screw extruder. Bicomponent fibers with a sheath/core (1/1) structure were prepared using this blend as the sheath component and polypropylene having a melt flow rate of 80 g/10 min (Chisso Corporation) as the core material. The spinning was conducted on a pilot scale bicomponent spinning line using two identical extruders, having the same specifications identified in Example 6, feeding into a sheath/core bicomponent spin pack and through 350 holes of 0.6 mm diameter. Likewise, the fibers were quenched and drawn down at 17° C. to form filaments of 3.4–3.8 denier/filament. Concentric sheath/core fibers having a light crimp were cut to a length of 6 mm. The bicomponent fibers, designated WDF-02, were then used as binder fibers to make a nonwoven fabric.

A nonwoven fabric was produced by blending 40 wt % Novalis (Lyon, France) nylon 6/6 staple fibers (6 mm cut length), 17 wt % conventional Hoechst-Celanese T-255 bicomponent binder fibers containing a "tackified" polyolefin sheath and a polyester core, and 43 wt % of the WDF-02 binder fibers. The T-255 binder fibers were added to further enhance the in-use strength of the nonwoven fabric, while maintaining ion triggerability of the fabric. The blend of fibers was passed through a Dan-web machine at a temperature of 145° C. to air bond the fibers. The fibers were further compacted using an embossing roll at a temperature of 110° C. and 6.5 bar pressure to produce a 32 grams/square meter (basis weight) nonwoven using the Dan-web forming process. Measured tensile strengths of the nonwoven fabric in the machine and cross machine directions were 638 grams and 329 grams per 50 mm width, respectively. After immersion in a solution containing one weight percent anhydrous sodium sulfate for 5 minutes, the machine and cross machine direction tensile strengths were found to be 124 grams and 62 grams per 50 mm width, respectively.

The nonwoven coverstock was placed in a diaper as a body side liner and repeatedly insulted with 50 milliliters of saline solution (0.85% sodium chloride, by weight) for a total of 150 milliliters over a one hour period in an abrasion test. The body side liner was found to survive the abrasion test without pilling, delamination (from construction adhesive), or formation of holes and tears.

EXAMPLE 9

A nonwoven fabric was produced by blending 40 wt % Novalis nylon 6/6 staple fibers (6 mm cut length), 20 wt % T-255 bicomponent binder fibers, and 40 wt % of the WDF-02 binder fibers. The blend of fibers was passed through a Dan-web machine at a temperature of 145° C. to air bond the fibers. The fibers were further compacted using an embossing roll at a temperature of 110° C. and 6.5 bar pressure to produce a 30 g/m$^2$ nonwoven using the Dan-web forming process. Measured tensile strengths in the machine and cross machine directions were 739 grams and 584 grams per 50 mm width, respectively. After immersion in a solution containing one weight percent anhydrous sodium sulfate for 5 minutes, the machine and cross machine direction tensile strengths were found to be 309 grams and 263 grams per 50 mm width, respectively. When the material first soaked in sodium sulfate solution was then subsequently placed in deionized water for a period of 14 hours, the machine direction tensile strength was found to be 239 grams per 50 mm width.

EXAMPLE 10

A nonwoven fabric was produced by blending 40 wt % Novalis nylon 6/6 staple fibers (6 mm cut length), 15 wt % T-255 bicomponent binder fibers, and 45 wt % of the WDF-02 binder fibers. The blend of fibers was passed through a Dan-web machine at a temperature of 145° C. to air bond the fibers. The fibers were further compacted using an embossing roll at a temperature of 110° C. and 6.5 bar pressure to produce a 29 g/m$^2$ nonwoven using the Dan-web forming process. Measured tensile strengths in the machine and cross machine directions were 715 grams and 668 grams per 50 mm width, respectively. After immersion in a solution containing one weight percent anhydrous sodium sulfate for 5 minutes, the machine and cross machine direction tensile strengths were found to be 145 grams and 163 grams per 50 mm width, respectively. When the material first soaked in sodium sulfate solution was then subsequently placed in deionized water for one hour, the machine direction tensile strength was found to be 84 grams per 50 mm width.

EXAMPLE 11

A nonwoven fabric was produced by blending 40 wt % Courtaulds (U.K.) LYOCELL™ fibers (3 denier/filament, 6 mm cut length), 20 wt % T-255 bicomponent binder fibers, and 40 wt % of the WDF-02 binder fibers. The blend of fibers was passed through a Dan-web machine at a temperature of 145° C. to air bond the fibers. The fibers were further compacted using an embossing roll at a temperature of 110° C. and 6.5 bar pressure to produce a 30 g/m$^2$ nonwoven using the Dan-web forming process. Measured tensile strengths in the machine and cross machine directions were 333 grams and 245 grams per 50 mm width, respectively. After immersion in a solution containing one weight percent anhydrous sodium sulfate for 5 minutes, the machine and cross machine direction tensile strengths were found to be 193 grams and 146 grams per 50 mm width, respectively. When the material first soaked in sodium sulfate solution was then subsequently placed in deionized water for one hour, the machine direction tensile strength was found to be 121 grams per 50 mm width.

EXAMPLE 12

A nonwoven fabric was produced by blending 40 wt % polyethylene terephthalate (PET) staple fibers from MiniFibers Inc. (Johnson City, Tenn.) (3 denier/filament, 6 mm cut length), 20 wt % T-255 bicomponent binder fibers, and 40 wt % of the WDF-02 binder fibers. The blend of fibers was passed through a Dan-web machine at a temperature of 145° C. to air bond the fibers. The fibers were further compacted using an embossing roll at a temperature of 110° C. and 6.5 bar pressure to produce a 25 g/m$^2$ nonwoven using the Dan-web forming process.

EXAMPLE 13

A nonwoven absorbent structure was produced by blending 70 wt % Weyerhauser (Federal Way, Wash.) NB416 pulp fibers, 3 wt % T-255 bicomponent binder fibers, and 27 wt % of the WDF-02 binder fibers. The blend of fibers was passed through a Dan-web machine at a temperature of 145° C. to air bond the fibers to form a 120 g/m$^2$ absorbent web using the Dan-web forming process. Measured cohesion ("z" direction strength) of the web was 0.31 kilograms. The web dispersed in ordinary tap water.

EXAMPLE 14

A nonwoven absorbent structure was produced by blending 70 wt % Weyerhauser NB416 pulp fibers, 6 wt % T-255 bicomponent binder fibers, and 24 wt % of the WDF-02 binder fibers. The blend of fibers was passed through a Dan-web machine at a temperature of 145° C. to air bond the fibers to form a 120 g/m$^2$ absorbent web using the Dan-web forming process. Measured cohesion ("z" direction strength) of the web was 0.53 kilograms. The web dispersed very slowly in ordinary tap water.

EXAMPLE 15

A nonwoven absorbent structure was produced by blending 70 wt % Weyerhauser NB416 pulp fibers, 5 wt % T-255 bicomponent binder fibers, and 25 wt % of the WDF-02 binder fibers. The blend of fibers was passed through a Dan-web machine at a temperature of 145° C. to air bond the fibers to form a 118 g/m$^2$ absorbent web using the Dan-web forming process. Measured cohesion ("z" direction strength) of the web was 0.43 kilograms. Measured tensile strengths in the machine and cross machine directions were 417 grams and 472 grams/50 mm width, respectively. The web dispersed slowly in ordinary tap water.

EXAMPLE 16

A nonwoven intake (surge) absorbent structure was produced by blending 35 wt % Weyerhauser NB416 pulp fibers, 35 wt % polyethylene terephthalate (PET) staple fibers from MiniFibers Inc. (6 denier/filament, 6 mm cut length), 5 wt % T-255 bicomponent binder fibers, and 25 wt % of the WDF-02 binder fibers. The blend of fibers was passed through a Dan-web machine at a temperature of 145° C. to air bond the fibers to form a 120 g/m$^2$ body fluid intake web using the Dan-web forming process. Measured cohesion ("z" direction strength) of the web was 0.33 kilograms. The body fluid intake web has a bulk thickness of 59 mils (1.5 mm), a density of 0.084 grams per cubic centimeter, a void volume of 12 cubic centimeters per gram, and an air porosity of 327 cubic feet per minute.

EXAMPLE 17

(Blown Film 80:20 blend)

A blend of copolyester NS 70-4442 and PLA (CPX 5-2) in a 80:20 ratio was compounded with a twin screw-extruder. The resulting resin was measured to have a melt index of 58 g/10 min at 160° C. (based on ASTMD 1238). Blown films of the resulting resin were prepared using a standard blown film machine. The extruder on the machine was operated under the following temperature profile: (1) the feed zone temperature: 180° F. (82.2° C.); (2) the barrel zone temperature: 210° F. (98.9° C.); (3) the adapter temperature: 230° F. (110.0° C.); and (4) the die temperature: 250° F. (121.1° C.). Uniform blown films were obtained under these process conditions.

EXAMPLE 18

(Control Blown Film: non-modified)

Blown films of 100% copolyester NS 70-4442 resin were unable to be prepared using the blown film machine and process conditions of Example 17. The resin had a very poor melt strength and was too sticky to be processed into a film.

The above disclosed examples are preferred embodiments and are not intended to limit the scope of the present invention in any way. Various modifications and other embodiments and uses of the disclosed water-sensitive compositions, apparent to those of ordinary skill in the art, are also considered to be within the scope of the present invention.

What is claimed is:

1. A multicomponent fiber comprising at least one water-sensitive polymer blended with at least one additional polymer, the at least one additional polymer being a polylactide, a polyolefin-grafted with one or more polar groups, or a second aliphatic polyester; wherein the water-sensitive polymer is ion triggerable.

2. The multicomponent fiber of claim 1, wherein the at least one water-sensitive polymer comprises a copolyester, a copolymer or terpolymer of acrylic acid, a copolymer or terpolymer of acrylate ester, or a blend thereof.

3. The multicomponent fiber of claim 1, wherein the weight ratio of the water-sensitive polymer to the at least one additional polymer is from about 60:40 to about 90:10.

4. The multicomponent fiber of claim 3, wherein the weight ratio of the water-sensitive polymer to the at least one additional polymer is from about 70:30 to about 80:20.

5. The multicomponent fiber of claim 1, wherein the multicomponent fiber is a sheath/core fiber, wherein the water-sensitive polymer and the at least one additional polymer is present in the sheath of the multicomponent fiber.

6. The multicomponent fiber of claim 5, wherein the core comprises a polymeric material having a melting temperature about 20° C. or greater than the melting temperature of the sheath.

7. The multicomponent fiber of claim 1, wherein the polylactide comprises a linear polylactide, a branched polylactide, a copolymer of optical isomers of lactide, a copolymer of lactide and caprolactone, or a blend thereof.

8. The multicomponent fiber of claim 1, wherein the one or more polar groups comprise maleic anhydride, polyethylene glycol, polyethylene glycol methacrylate, hydroxyethyl methacrylate, 2-ethylhexyl methacrylate, vinyl alcohol, vinyl acetate, or combinations thereof.

9. The multicomponent fiber of claim 1, wherein the second aliphatic polyester comprises polybutylene succinate, polybutylene succinate-co-adipate, polycaprolactone, or a blend thereof.

10. The multicomponent fiber of claim 1, wherein the fiber remains stable when in contact with a 1 wt % sodium sulfate solution, but dissolve when placed in contact with deionized water.

11. The multicomponent fiber of claim 1, wherein the at least one water-sensitive polymer comprises one or more sulfonate groups, carboxylate groups, or a blend thereof.

12. The multicomponent fiber of claim 1, wherein the water-sensitive polymer and the at least one additional polymer are present on an outer surface of the fiber.

13. The multicomponent fiber of claim 1, wherein the at least one additional polymer is a polylactide copolymer having a similar melt viscosity to the water-sensitive polymer.

14. The multicomponent fiber of claim 4, wherein the weight ratio of the water-sensitive polymer to the at least one additional polymer is from about 75:25 to about 85:15.

15. The multicomponent fiber of claim 6, wherein the polymeric material comprises polypropylene, polyethylene, or a combination thereof.

16. A multicomponent fiber comprising at least one water-sensitive polymer blended with at least one additional polymer, wherein the water-sensitive polymer is ion triggerable and the at least one additional polymer is not ion triggerable, and wherein the weight ratio of the water-sensitive polymer to the at least one additional polymer is from about 60:40 to about 90:10.

17. The multicomponent fiber of claim 16, wherein the fiber remains stable when in contact with a 1 wt % sodium sulfate solution, but dissolve when placed in contact with deionized water.

18. The multicomponent fiber of claim 16, wherein the water-sensitive polymer and the at least one additional polymer are present on an outer surface of the fiber.

19. The multicomponent fiber of claim 16, wherein the multicomponent fiber is a sheath/core fiber, and wherein the water sensitive polymer and the at least one additional polymer are present in the sheath of the multicomponent fiber.

20. A multicomponent fiber comprising a water-sensitive copolyester blended with a polylactide, wherein the multicomponent fiber is ion triggerable.

21. The multicomponent fiber of claim 20, wherein the fiber remains stable when in contact with a 1 wt % sodium sulfate solution, but dissolve when placed in contact with deionized water.

22. The multicomponent fiber of claim 20, wherein the water-sensitive polymer and the at least one additional polymer are present on an outer surface of the fiber.

* * * * *